United States Patent
Scherschlicht et al.

[11] Patent Number: 5,326,769
[45] Date of Patent: Jul. 5, 1994

[54] (S)-1-[(10-CHLORO-6,7-DIHYDRO-4-OXO-3-PHENYL-4H-BENZO[A]QUINO-LIZIN-1-YL)CARBONYL]-3-ETHOXYPYRROLIDINE

[75] Inventors: Richard R. Scherschlicht, Inzlingen, Fed. Rep. of Germany; Ulrich Widmer, Rheinfelden, Switzerland

[73] Assignee: Hoffmann-La Roche Inc., Nutley, N.J.

[21] Appl. No.: 36,295

[22] Filed: Mar. 24, 1993

Related U.S. Application Data

[62] Division of Ser. No. 818,653, Jan. 6, 1992, Pat. No. 5,281,711.

[30] Foreign Application Priority Data

Jan. 25, 1991 [CH] Switzerland .............. 228/91

[51] Int. Cl.$^5$ .................. A61K 31/435; C07D 221/04
[52] U.S. Cl. .................... 514/294; 514/923; 546/95
[58] Field of Search ............ 546/95; 514/294, 923

[56] References Cited

U.S. PATENT DOCUMENTS 4,889,848 12/1989 Fischer et al. .................. 514/212

FOREIGN PATENT DOCUMENTS 183994. 6/1986 European Pat. Off. .
304087 2/1989 European Pat. Off. .

OTHER PUBLICATIONS

Fischer et al., "Tricyclic pyridine derivatives with high affinity to the central benzodiazepine receptor", Helv. Chim. Acta 73:763–781 (1990).
Tamasawa et al., "Stereoselectivity of a potent calcium antagonist, 1-benzyl-3-pyrrolidinyl methyl 2,6-dimethyl-4-(m-nitrophenyl)-1,4-dihydropyridine-3,5-dicarboxylate", J. Med. Chem. 29:2504–2511 (1986).
Bhat et al., "Synthetic routes to chiral 3-pyrrolidinols", Synth. Comm. 15:587–598 (1985).
Scherschlicht et al., "Effects of oral and intravenous midazolam, triazolam and flunitrazepam on the sleep-wakefulness cycle of rabbits", Br. J. Clin. Pharmac. 16:29S–35S (1983).
Chemical Abstracts Service, CA 107:134200, 1986.

*Primary Examiner*—Marianne M. Cintins
*Assistant Examiner*—Catherine S. Kilby Scalzo
*Attorney, Agent, or Firm*—George M. Gould; George W. Johnston; Robert A. Silverman

[57] ABSTRACT

The compound (S)-1-[(10-chloro-6,7-dihydro-4-oxo-3-phenyl-4H-benzo[a]quino-lizin-1-yl)carbonyl]-3-ethoxypyrrolidine of the formula

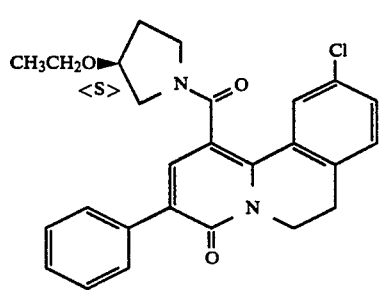

which has valuable pharmacological properties, is described. In particular, the compound of formula I has a non-sedating, hypnotic, that is, sleep-promoting, activity and can accordingly be used for the treatment of sleep disorders.

4 Claims, No Drawings

(S)-1-[(10-CHLORO-6,7-DIHYDRO-4-OXO-3-PHENYL-4H-BENZO[A]QUINO-LIZIN-1-YL)CARBONYL]-3-ETHOXYPYRROLIDINE

This is a division, of application Ser. No. 07/818,653 filed Jan. 6, 1992, now U.S. Pat. No. 5,281,711, issued Jan. 25, 1994.

BRIEF SUMMARY OF THE INVENTION

The invention relates to the compound (S)-1-[(10-chloro-6,7-dihydro-4-oxo-3-phenyl-4H-benzo[a]quinolizin-1-yl)carbonyl]-3-ethoxypyrrolidine of the formula

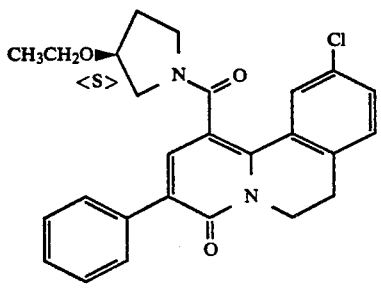

I

The compound of formula I has valuable pharmacological properties and can be used for the treatment or prevention of illnesses. In particular, it has a non-sedating, hypnotic, that is, sleep-promoting, activity and can therefore be used for the treatment of sleep disorders.

DETAILED DESCRIPTION OF THE INVENTION

The invention relates to the compound (S)-1-[(10-chloro-6,7-dihydro-4-oxo-3-phenyl-4H-benzo[a]quinolizin-1-yl)carbonyl]-3-ethoxypyrrolidine of the formula

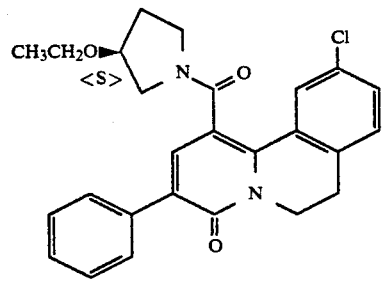

I

The compound of formula I has valuable pharmacological properties and is useful for the treatment or prevention of illnesses. In particular, it has a non-sedating, hypnotic, that is, sleep-promoting, activity and can therefore be used for the treatment of sleep disorders.

Objects of the invention are the compound of formula I and its use as a therapeutically active substance; a process for its preparation; medicaments containing the compound of formula I and the preparation of these medicaments; the use of the compound of formula I in the treatment or prevention of illnesses and for the preparation of medicaments for the treatment of sleep disorders; as well as a method for the treatment of patients suffering from sleep disorders.

The racemate corresponding to the compound of formula I, its preparation and its anticonvulsive properties are described in European Patent Publication No. 183,994. In this Publication, it is stated that the racemate has muscle relaxing, sedative hypnotic and anxiolytic properties.

The compound of formula I can be prepared by converting the carboxylic acid of the formula

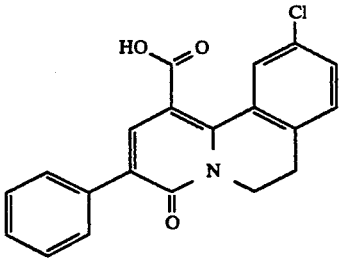

II or a reactive derivative thereof into the corresponding amide with an amine of the formula

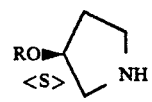

III wherein R is hydrogen or ethyl, and, when R is hydrogen, alkylating the resulting compound of the formula

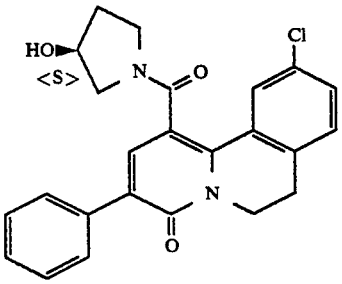

IV with an agent which yields an ethyl group.

The reaction of the carboxylic acid of formula II with an amine of formula III is preferably carried out in the presence of a condensation agent such as O-benzotriazol-1-yl-N,N,N',N'-tetramethyluronium hexafluorophosphate or N-methyl-2-chloropyridinium iodide, in an inert organic solvent and in the presence of a base. Suitable solvents are, for example, aromatic hydrocarbons such as benzene, toluene and xylene and N,N-dimethylformamide. Suitable bases are, for example, tertiary amines such as triethylamine, 4-methylmorpholine and the like. A preferred carboxylic acid derivative, which can be reacted directly with the amine of formula III in the presence of a base, is the corresponding carboxylic acid chloride. Suitable bases are, in turn, the aforementioned tertiary amines. Suitable solvents are, for example, aromatic hydrocarbons such as benzene, toluene and xylene and ethers such as dioxane. In both cases, the reaction is preferably carried out at a temperature in the range of from room temperature to the reflux temperature of the reaction mixture.

When R, in the amine of formula III, is hydrogen, then there is initially obtained the compound of formula IV which is subsequently alkylated to the compound of formula I with an agent yielding an ethyl group. This alkylation is conveniently carried out in an inert organic solvent such as N,N-dimethylformamide or the like, with a strong base, for example, an alkali metal hydride or hydroxide such as sodium hydride, potassium hydroxide and sodium hydroxide conveniently being used as the base. The reaction is conveniently carried out at a temperature in the range of from about 0° C. to room temperature. An ethyl halide, especially ethyl iodide or ethyl bromide, or diethyl sulfate is preferably used as the alkylating agent.

The compound of formula IV is also part of the invention.

The compound of formula III, in which R is hydrogen, which is used as the starting material, is a known compound; see European Patent Publication No. 304,087, page 11.

The compound of formula III, in which R is ethyl, which is used as the starting material, can be prepared, for example, by alkylating (S)-1-benzyl-3-pyrrolidinol with an ethyl halide such as ethyl bromide and ethyl iodide in the presence of a base and subsequently cleaving the benzyl group by catalytic hydrogenolysis. (S)-1-Benzyl-3-pyrrolidinol is also a known compound; see J. Med. Chem. 29, 2504–2511 (1986) and Synth. Comm. 15, 587–598 (1985).

Sleep-inducing medicaments, previously used for example, barbiturates and benzodiazepines, are medicaments having sedative-hypnotic activity. These medicaments act not only as hypnotics, that is, sleep-promoting, but also as sedatives. Their use therefore leads to a general, unspecific lowering of vigilance which manifests itself, for example, in the cognitive, amnestic, reactive, sensor and motoric capacity being restricted even in the waking state. Under certain circumstances, this leads to dangerous situations in the period between consumption and onset of sleep as well as in the case of an interruption in sleep at the point when they are fully effective. Non-sedating hynotics are accordingly substances which induce and maintain sleep, but which do not influence or influence only immaterially the functions of the central nervous system in the waking state.

It has now surprisingly been found that the compound of formula I does have hypnotic activity, but not sedative activity, and, therefore, does not possess the known disadvantages of the sedative-hypnotic sleep-inducing medicaments.

The sleep-inducing activity of the compound of formula I can be demonstrated in the test utilizing rabbits as described hereinafter. The animals are provided, under complete narcosis, with electrodes in regions of the brain whose amplified electrical signals (electroencephalogram, EEG) permit the differentiation of wakefulness (W), non-REM sleep (NREMS) and REM sleep (REMS). REM sleep is dream sleep; it is so named because during such sleep rapid eye movements (Rapid Eye Movements) occur. The electrodes are connected to a plug which is fastened to the skull so that during the test the electrodes can be connected via a cable with the amplifiers and the recording device. After the wound has healed, the animals are housed in soundproofed boxes for two days. The EEG's are registered (see Scherschlicht and Marias in Brit. J. Clin. Pharmacol. 16, 29S–35S [1983] during these two days in each case at 9 and 15 hours. On the first day a vehicle (control) is administered perorally to the experimental animals and on the second day 0.1, 0.3, 1 or 10 mg/kg of the compound of formula I is administered perorally. Four animals are used per dosage. Since, in contrast to human beings, rabbits do not sleep continuously, the time spent in NREMS and REMS is added up and expressed per hour as a % of 60 minutes. The results determined are compiled in the following Table.

The results show that the compound of formula I in all dosages used increases time spent in NREMS to 70–75% of the first hour of the recording of sleep. Thereafter, the time in NREMS falls away variably and rapidly. The higher the dosage used, the longer is this activity maintained. On the other hand, on the control days the animals spend about 50% of each hour in NREMS. The lowest value is found in each case in the first hour of the recording. The compound of formula I exhibits no influence on the REMS.

TABLE

| NREMS | 0.1 mg/kg p.o. | | 0.3 mg/kg p.o. | | 1 mg/kg p.o. | | 10 mg/kg p.o. | |
|---|---|---|---|---|---|---|---|---|
|  | C | S | C | S | C | S | C | S |
| 1st hour | 40.8 | 75.9* | 39.0 | 70.3* | 43.8 | 73.9* | 46.6 | 72.8* |
| 2nd hour | 51.2 | 63.0 | 40.7 | 69.8* | 46.7 | 66.0* | 47.0 | 70.8* |
| 3rd hour | 49.5 | 55.3 | 43.9 | 53.3 | 54.5 | 64.1* | 47.7 | 72.5* |
| 4th hour | 45.0 | 60.1 | 55.9 | 65.4 | 49.7 | 59.3 | 48.2 | 68.3* |
| 5th hour | 64.1 | 52.5 | 44.7 | 44.5 | 57.4 | 67.6 | 48.1 | 61.6 |
| 6th hour | 46.4 | 56.2 | 41.5 | 62.0 | 60.4 | 66.4 | 46.1 | 69.5* |

The values are % of each hour (average from four tests per dosage).
*Significant difference to the control value ($p < 0.05$).
C: control; S: test substance; NREMS: non-REM sleep; REMS: sleep with rapid eye movements.

The non-sedating activity of the compound of formula I can be demonstrated, for example, in the Horizontal Wire Test (HWT). In this test, mice or rats are held by the tail and lifted up so that they can catch hold of a horizontally stretched wire with the front feet. When released, normal animals immediately arch up and also grip the wire with the hind feet. Substances with sedative activity, depending on the degree of sedation, cause the animals to remain hanging motionless or to fall from the wire. The compound of formula I is administered perorally to the experimental animals and in dosages up to 300 mg/kg does not show a sedating activity either in mice or rats. The treated experimental animals behave as the untreated, normal animals.

The compound of formula I can be used as a medicament, for example, in the form of pharmaceutical preparations. The pharmaceutical preparations can be administered perorally, for example, in the form of tablets, coated tablets, dragées, hard and soft gelatin capsules, solutions, emulsions or suspensions. The administration can, however, also be effected rectally, for example, in the form of suppositories, or parenterally, for example, in the form of injections.

For the preparation of pharmaceutical compositions, the product in accordance with the invention can be processed with pharmaceutically inert, inorganic or organic carriers. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. No carriers are generally required in the case of soft gelatin capsules. Suitable carriers for the preparation of solutions and syrups are, for example, water, polyols, saccharose, invert sugar, glucose and the like. Suitable carriers for injections are, for example, water, alcohols, polyols, glycerol, vegetable oils and the like. Suitable carriers for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, coating agents and/or anti-oxidants. They can also contain still other therapeutically valuable substances. Medicaments containing the compound of formula I in accordance with the invention and a therapeutically inert carrier as well as a process for their preparation, which comprises bringing the compound of formula I in accordance with the invention and, if desired, another therapeutically active substance into a galenical administration form, are also objects of the invention.

As already mentioned, the compound of formula I in accordance with the invention can be used in the treatment or prevention of illnesses, especially in the treatment of sleep disorders, as well as for the preparation of medicaments with non-sedating hypnotic properties. The dosage can vary within wide limits and will, of course, be fitted to the individual requirements in each particular case. In the case of oral administration, the effective dosage lies in a range of about 0.1 mg to about 100 mg, preferably of about 0.5 mg to about 20 mg.

The Examples which follow illustrate the invention in more detail. All temperatures are given in degrees Celsius.

EXAMPLE 1 a) 70.36 g of 10-chloro-6,7-dihydro-4-oxo-3-phenyl-4H-benzo[a]quinolizine-1-carboxylic acid are dissolved in 1600 ml of N,N-dimethylformamide under argon, whereupon 45 ml of 4-methylmorpholine, 27.2 g of (S)-3-hydroxypyrrolidine hydrochloride and 83.4 g of O-benzotriazol-1-yl-N,N,N',N'-tetramethyluronium hexafluorophosphate are added in succession. The mixture is stirred at room temperature for about 18 hours and the yellow solution obtained is poured into 6000 ml of water and treated slowly with 2500 ml of saturated sodium hydrogen carbonate solution. The product obtained is filtered under suction and washed with 1000 ml of water. After drying in a vacuum at 70° there are obtained 83.3 g of crude product. By repeated recrystallization from a 120-fold amount of isopropanol and chromatography of the combined mother liquours on 1000 g of silica gel with methylene chloride/diethyl ether (9:1) and subsequently with methylene chloride/acetone (9:1), there are obtained 74.2 g (88%) of (S)-1-[(10-chloro-6,7-dihydro-4-oxo-3-phenyl-4H-benzo[a]quinolizin-1-yl)carbonyl]-3-hydroxypyrrolidine with a m.p. of 257°–259°.

b) 64.3 g of (S)-1-[(10-chloro-6,7-dihydro-4-oxo-3-phenyl4H-benzo[a]quinolizin-1-yl)carbonyl]-3-hydroxypyrrolidine are dissolved in 900 ml of N,N-dimethylformamide by slight heating (44°). The solution is then cooled to 13°, treated with 31 ml of ethyl iodide and cooled to 3°–5°. After the addition of 17.1 g of powdered potassium hydroxide, the mixture is stirred at about 0° for 5 hours. The reaction mixture is then poured into 8000 ml of water and acidified with 50 ml of 25 percent hydrochloric acid. The suspension is stirred at room temperature overnight. The crystals are then filtered under suction, washed with water and dried at 80° in a vacuum. By chromatography of the material obtained on 3000 g of silica gel with methylene chloride/diethyl ether (9:1), (4:1), (3:1) and (2:1), there are obtained 58.5 g of crude product and 4.4 g of a mixture, which is recrystallized from isopropanol. There are thus obtained 3.75 g of a not quite pure product which is recrystallized from isopropanol together with the previously obtained crude product. There are obtained a total of 54.7 g (80%) of (S)-1-[(10-chloro-6,7-dihydro-4-oxo-3-phenyl-4H-benzo[a]quinolizin-1-yl)carbonyl]-3-ethoxypyrrolidine with a m.p. of 144°–147°.

EXAMPLE 2 a) 5 g of sodium hydride (60%) are suspended in 100 ml of dry tetrahydrofuran. 10 ml of (S)-1-benzyl-3-pyrrolidinol are then slowly added dropwise at 0° C. After completion of the addition the mixture is stirred at room temperature until the hydrogen evolution has finished. Subsequently, the mixture is stirred for a further hour. It is cooled to 0° C. and 9.75 ml of ethyl iodide are then slowly added dropwise. The mixture is left to warm to room temperature and is stirred overnight. 50 ml of methanol are added thereto while cooling with ice in order to destroy excess sodium hydride. The reaction mixture is concentrated in a vacuum and the residual oil is taken up in 200 ml of methylene chloride and extracted twice with 100 ml of saturated sodium chloride solution each time. The organic phase is dried over sodium sulphate and subsequently concentrated in a vacuum. 14 g of a yellow oil are obtained. The crude product is chromatographed on 140 g of silica gel with hexane/ethyl acetate (2:1). 9.3 g (75%) of (S)-1-benzyl-3-ethoxypyrrolidine are obtained as a yellowish oil.

b) 10 g of (S)-1-benzyl-3-ethoxypyrrolidine are dissolved in 100 ml of methanol, treated with 1 g of 10% palladium-on-charcoal and stirred under a hydrogen atmosphere. Uptake of hydrogen no longer takes place after 4 hours. The catalyst is filtered off over a Dicalite pad and the residue is concentrated in a vacuum. 5.3 g (95%) of (S)-3-ethoxypyrrolidine are obtained as a yellow oil.

c) 7.04 g of 10-chloro-6,7-dihydro-4-oxo-3-phenyl-4H-benzo[a]quinolizine-1-carboxylic acid are suspended in 100 ml of ethyl acetate under argon and treated with 2.1 ml of oxalyl chloride. Subsequently, 0.2 ml of N,N-dimethylformamide is added, whereby an evolution of gas is observed. The mixture is left to stir at room temperature for 30 minutes, a further 0.2 ml of oxalyl chloride and thereupon 0.1 ml of N,N-dimethylformamide are added thereto and the mixture is left to stir at room temperature for a further 30 minutes. The reaction mixture is cooled to 0°–5° C. in an ice bath, whereby crystals separate. 13.3 ml of triethylamine are added and a solution of 2.53 g of (S)-3-ethoxypyrrolidine in 25 ml of ethyl acetate is subsequently added dropwise. The mixture is subsequently stirred at about 0° C. for 30 minutes, washed twice with 50 ml of water each time and the combined aqueous phases are extracted once with 20 ml of ethyl acetate. The combined organic phases are dried over sodium sulphate, filtered and evaporated, whereby 9.0 g of crude product are obtained. The crude product is dissolved in 50 ml of methylene chloride and filtered through 45 g of silica gel (methylene chloride/acetone 9:1), whereby 8.6 g of yellow crystals are obtained. These are taken up in 100 ml of tert.-butyl methyl ether and heated to reflux for 1 hour. The mixture is left to cool to room temperature and the crystals (6.95 g) are filtered off under suction. 5.5 g of the thus-obtained crude product are recrystallized from 55 ml of ethyl acetate, whereby, for crystallization, the mixture is cooled in an ice bath. After drying at 80° C./0.05 mm (18 hrs.) there are obtained 4.2 g of (S)-1-[(10-chloro-6,7-dihydro-4-oxo-3-phenyl-4H-benzo[a]quinolizin-1-yl)carbonyl]-3-ethoxypyrrolidine of m.p. 134°–136° C.

EXAMPLE A

The compound of formula I can be used in a known manner as the active substance for the preparation of pharmaceutical dosage forms of the following composition:

| Tablets | mg/tablet |
|---|---|
| Active substance | 5 |
| Lactose | 135 |
| Corn starch | 51 |
| Polyvinylpyrrolidone | 8 |
| Magnesium stearate | 1 |
| Tablet weight | 200 |

| Capsules | mg/capsules |
|---|---|
| Active substance | 10 |
| Lactose | 30 |
| Corn starch | 8.5 |
| Talc | 1 |
| Magnesium stearate | 0.5 |
| Capsule fill weight | 50 |

We claim:

1. A pharmaceutical composition for treating sleep disorders which comprises an effective amount of (S)-1-[(10-chloro-6,7-dihydro-4-oxo-3-phenyl-4H-benzo[a]-quinolizin-1-yl)carbonyl]-3-ethoxypyrrolidine and a therapeutically inert carrier material.

2. A pharmaceutical composition in accordance with claim 1, wherein the effective amount is in the range of from about 0.1 mg to about 100 mg.

3. A method of treating sleep disorders which comprises administering to a host in need of such treatment an effective amount of (S)-1-[(10-chloro-6,7-dihydro-4-oxo-3-phenyl-4H-benzo[a]quinolizin-1-yl)carbonyl]-3-ethoxypyrrolidine.

4. A method in accordance with claim 3, wherein the effective amount is in the range of from about 0.1 mg to about 100 mg.

* * * * *